United States Patent [19]
Pollak et al.

[11] Patent Number: 5,659,041
[45] Date of Patent: Aug. 19, 1997

[54] HYDRAZINO-TYPE RADIONUCLIDE CHELATORS HAVING AN $N_3S$ CONFIGURATION

[75] Inventors: Alfred Pollak, Toronto; Robert A. Kirby, Acton; Robert Dunn-Dufault, Bramalea, all of Canada

[73] Assignee: Resolution Pharmaceuticals, Inc., Mississauga, Canada

[21] Appl. No.: 299,636

[22] Filed: Sep. 2, 1994

Related U.S. Application Data

[63] Continuation-in-part of Ser. No. 92,911, Jul. 19, 1993, abandoned.

[51] Int. Cl.⁶ ............ C07D 213/77; C07D 213/80; C07D 237/20; C07D 239/42
[52] U.S. Cl. ............ 546/306; 546/153; 546/139; 546/141; 546/159; 546/156; 546/143; 534/10; 534/14; 530/391.5; 564/310; 564/226; 544/180; 544/239; 544/240; 544/194
[58] Field of Search ............ 424/1.65; 544/224, 544/230, 239, 180, 240, 194, 264, 276, 336, 407, 298, 322, 344; 546/306, 153, 156, 159, 139, 141, 143; 548/326.5, 483, 545, 546, 367.4, 371.7, 531, 542, 558, 225, 233, 182, 190; 534/10, 14; 530/391.5

[56] References Cited

U.S. PATENT DOCUMENTS

| | | | |
|---|---|---|---|
| 4,732,864 | 3/1988 | Tolman | 436/547 |
| 4,849,511 | 7/1989 | Verbruggen | 534/14 |
| 4,861,869 | 8/1989 | Nicolotti et al. | 530/402 |
| 4,897,255 | 1/1990 | Fritzberg et al. | 424/1.1 |
| 4,965,392 | 10/1990 | Fritzberg et al. | 558/254 |
| 4,980,147 | 12/1990 | Fritzberg et al. | 424/1.1 |
| 5,037,630 | 8/1991 | Fritzberg et al. | 424/1.1 |
| 5,082,930 | 1/1992 | Nicolotti et al. | 530/402 |
| 5,089,249 | 2/1992 | Fritzberg et al. | 424/1.1 |
| 5,091,514 | 2/1992 | Fritzberg et al. | 534/14 |
| 5,095,111 | 3/1992 | Lever et al. | 540/544 |
| 5,112,594 | 5/1992 | Woulfe et al. | 424/1.1 |
| 5,112,595 | 5/1992 | Woulfe et al. | 424/1.1 |
| 5,112,953 | 5/1992 | Gustavson et al. | 530/391.5 |
| 5,120,526 | 6/1992 | Fritzberg et al. | 424/1.1 |
| 5,175,257 | 12/1992 | Kasina et al. | 530/391.5 |
| 5,175,343 | 12/1992 | Fritzberg et al. | 560/145 |
| 5,187,264 | 2/1993 | Verbruggen | 534/14 |
| 5,196,515 | 3/1993 | Lever et al. | 530/363 |
| 5,202,451 | 4/1993 | Fritzberg et al. | 556/419 |

FOREIGN PATENT DOCUMENTS

| | | |
|---|---|---|
| 33518/89 | 10/1991 | Australia . |
| 1317066 | 4/1993 | Canada . |
| 0 384 769 | 8/1990 | European Pat. Off. . |
| 89/07456 | 8/1989 | WIPO . |
| 90/06323 | 6/1990 | WIPO . |
| 91/16076 | 10/1991 | WIPO . |
| 92/10214 | 6/1992 | WIPO . |
| 92/10466 | 6/1992 | WIPO . |
| 92/10465 | 6/1992 | WIPO . |
| 92/13572 | 8/1992 | WIPO . |
| 92/19573 | 11/1992 | WIPO . |
| 92/19235 | 11/1992 | WIPO . |
| 92/19274 | 11/1992 | WIPO . |
| 92/21383 | 12/1992 | WIPO . |
| 93/02713 | 2/1993 | WIPO . |

OTHER PUBLICATIONS

Dewanjee, "The Chemistry of $^{99m}$Tc–labeled Radiopharmaceuticals", Seminars in Nuclear Medicine, vol. XX;5–27, (1990).

Green et al., "Gallium Radiopharmaceutical Chemistry", Nucl. Med. Biol. vol. 16:435–448, (1989).

Brenner et al., "Synthesis And Characterization Of A Series Of Isomeric Oxotechnetium(V) Diamido Dithiolates", Inorg. Chem., vol. 23:3793–3797, (1984).

Cotysyfakis et al., "Indium–111–labeled Cationic Complexes Of Aminothiols", Eur. J. Nucl. Med., vol. 20:302–307, (1993).

Eckelman et al., "Three Approaches To Radiolabeling Antibodies With $^{99m}$Tc", Nucl. Med. Biol., vol. 16(2):171–176, (1989).

Fischman et al., "Imaging Focal Sites Of Bacterial Infection In Rats With Indium–111–labeled Chemotactic Peptide Analogs", J. Nucl. Med., vol. 32:483–494, (1991).

Fritzberg et al., "Approaches To Radiolabeling Of Antibodies For Diagnosis And Therapy Of Cancer", Pharmaceutical Res., vol. 5(6):325–334. (1988).

Olsen, "Synthesis Of Quinoxaline Peptides By The Solid Phase Method", J. Heterocycl. Chem., vol. 7(2):435–437, (1970).

Paik et al., "The Labeling Of High Affinity Sites Of Antibodies With $^{99m}Tc$", Int. J. Nucl. Med. Biol., vol. 12:3–8, (1985).

Schneider et al., "N,N'–bis(S–benzoylmercaptoacetamido) Ethylenediamine And Propylenediamine Ligands As Renal Function Imaging Agents", J. Nucl. Med., vol. 25:223–229, (1984).

*Primary Examiner*—Gary E. Hollinden
*Assistant Examiner*—Michael G. Hartley
*Attorney, Agent, or Firm*—Foley & Lardner

[57] ABSTRACT

Radionuclide chelating compounds are provided for conjugation to targeting molecules such as proteins, peptides or antibodies. The resulting labeled targeting molecules may be used in diagnosis and therapy.

33 Claims, No Drawings

HYDRAZINO-TYPE RADIONUCLIDE CHELATORS HAVING AN N₃S CONFIGURATION

This application is a continuation-in-part of Ser. No. 08/092,911 filed Jul. 19, 1993, now abandoned.

FIELD OF THE INVENTION

This invention is in the field of diagnostic imaging, and relates to chemical chelators useful in the radiolabeling of agents that target tissues of diagnostic interest.

BACKGROUND OF THE INVENTION

The art of diagnostic imaging exploits contrasting agents that in binding or localizing site selectively within the body, help to resolve the image of diagnostic interest. $^{67}$Gallium salts, for example, have an affinity for tumours and infected tissue and, with the aid of scanning tomography, can reveal afflicted body regions to the physician. Other contrasting agents include the metal radionuclides such as $^{99m}$technetium and $^{186/188}$rhenium, and these have been used to label targeting molecules, such as proteins, peptides and antibodies that localize at desired regions of the human body.

As targeting agents, proteins and other macromolecules can offer the tissue specificity required for diagnostic accuracy; yet labeling of these agents with metal radionuclides is made difficult by their physical structure. Particularly, protein and peptide targeting agents present numerous sites at which radionuclide binding can occur, resulting in a product that is labeled heterogeneously. Also, and despite their possibly large size, proteins rarely present the structural configuration most appropriate for high affinity radionuclide binding, i.e. a region incorporating four or more donor atoms that form five-membered rings. As a result, radionuclides are bound typically at the more abundant low-affinity sites, forming unstable complexes.

To deal with the problem of background binding, Paik et al (Nucl Med Biol 1985, 12:3) proposed a method whereby labeling of antibody is performed in the presence of excess DPTA (diaminetrimethylenepentaacetic acid), to mask the low affinity binding sites. While the problem of low affinity binding is alleviated by this method, actual binding of the radionuclide, in this case technetium, was consequently also very low. The direct labeling of proteins having a high proportion of cysteine residues also has been demonstrated (Dean et al; WO 92/13,572). This approach exploits thiol groups of cysteine residues as high-affinity sites for radionuclide binding, and is necessarily limited in application to those targeting agents having the required thiol structure.

A promising alternative to the direct labeling of targeting agents is an indirect approach, in which targeting agent and radionuclide are conjugated using a chelating agent. Candidates for use as chelators are those compounds that bind tightly to the chosen metal radionuclide and also have a reactive functional group for conjugation with the targeting molecule. For use in labeling peptide and protein-based targeting agents, the chelator is ideally also peptide-based, so that the chelator/targeting agent conjugate can be synthesized in toto using peptide synthesis techniques. For utility in diagnostic imaging, the chelator desirably has characteristics appropriate for its in vivo use, such as blood and renal clearance and extravascular diffusibility.

SUMMARY OF THE INVENTION

The present invention provides chelators that bind diagnostically useful metal radionuclides, and can be conjugated to targeting agents capable of localizing at body sites of diagnostic and therapeutic interest. The chelators of the present invention are peptide analogs designed structurally to present an N₃S configuration capable of binding oxo, dioxo and nitrido ions of $^{99m}$technetium and $^{186/188}$rhenium.

More particularly, and according to one aspect of the invention, there are provided metal radionuclide chelators of the formula:

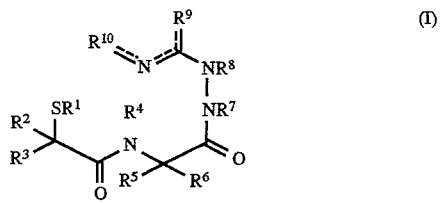

wherein
- $R^1$ is H or a sulfur protecting group;
- $R^2$ and $R^3$ are selected independently from H; carboxyl; lower alkyl; and lower alkyl substituted with a group selected from hydroxyl, sulfhydryl, halogen, carboxyl and aminocarbonyl;
- $R^4$ and $R^7$ are each H;
- $R^5$ and $R^6$ are selected independently from H; carboxyl; lower alkyl; lower alkyl substituted with a group selected from hydroxyl, sulfhydryl, halogen, carboxyl, lower alkoxycarbonyl and aminocarbonyl; and an alpha carbon side chain of any amino acid other than proline;
- $R^8$ is selected from H, carboxyl, lower alkyl and lower alkyl substituted with hydroxyl, carboxyl or halogen; and
- $R^9$ and $R^{10}$ together form a 5- or 6-membered, saturated or unsaturated heterocyclic ring which is optionally fused to another 5- or 6-roeinhered saturated or unsaturated, heterocyclic or carbocyclic ring wherein either ring is optionally substituted with a group selected from halogen, alkyl, hydroxyalkyl, carboxyl, carboxyalkyl, carboxyalkylthio, thiocyanato, amino, hydrazino and a conjugating group for coupling a targeting molecule to said either ring.

According to another aspect of the invention, the chelators of the above formula are provided in a form having the metal radionuclide complexed therewith.

In another aspect of the invention, there is provided a conjugate in which the chelator is provided in a form coupled to a diagnostically useful targeting molecule, and optionally in combination with a complexed metal radionuclide, for imaging use.

Another aspect of the invention provides a process for preparing chelators of the invention that are coupled to a diagnostically useful targeting molecule. In particular, the method employs solid phase peptide synthesis techniques to prepare chelator conjugates.

In another aspect of the invention, there is provided methods of imaging sites of inflammation with chelators of the invention coupled to a diagnostically useful targeting molecule in a form complexed with a traceable metal. In particular the targeting molecule is a peptide that localizes at sites of inflammation by binding to a particular receptor.

In yet another aspect of the invention, there is provided a method of imaging a site of inflammation within a mammal. The method involves the step of administering a compound that contains a diagnostically effective amount of a chelator of the invention coupled to a diagnostically useful targeting molecule in a form complexed with a traceable metal.

DETAILED DESCRIPTION OF THE INVENTION

The invention provides metal radionuclide chelators that when conjugated to a targeting molecule are useful for delivering a radionuclide to a body site of therapeutic or diagnostic interest. As illustrated in the above formula, the chelators are hydrazinc-type compounds that present an $N_3S$ configuration in which the radionuclide is complexed.

Terms defining the variables $R^1$–$R^{10}$ as used hereinabove have the following meanings:

"alkyl" refers to a straight or branched $C_1$–$C_8$ chain and embraces the term "lower alkyl" which refers to a straight or branched $C_1$–$C_3$ chain;

"halogen" refers to F, Cl and Br;

"sulfur protecting group" refers to a chemical group that inhibits oxidation, including those that are cleaved upon chelation of the metal. Suitable sulfur protecting groups include known alkyl, aryl, acyl, alkanoyl, aryloyl, mercaptoacyl and organothio groups.

In preferred embodiments of the invention, the chelators conform to the above formula in which:

$R^1$ is a hydrogen atom or a sulfur protecting group selected from benzoyl, acetamidomethyl and substituted or unsubstituted tetrahydropyranyl groups;

$R^2$ and $R^3$ are selected independently from H and a lower alkyl group selected from ethyl, propyl and most preferably methyl;

$R^4$ and $R^7$ are each H;

$R^5$ and $R^6$ are selected independently from H, carboxyl and lower alkyl which is preferably methyl; and $R^8$ is selected from H, carboxyl, and lower alkyl, preferably methyl.

In specific embodiments of the invention, the chelators conform to the above general formula wherein $R^1$ is H or a sulfur protecting group and $R^2$ through $R^8$ are each H.

Particular chelators include:
N(-S-benzoylmercaptoacetyl)-glycyl-2-pyridylhydrazide
N(-S-benzoylmercaptoacetyl)-L-glutamyl-(gamma-methyl ester)-2-pyridylhydrazide
N(-S-benzoylmercaptoacetyl)-glycyl-3-(6-chloropyridazyl)-hydrazide
N(-S-benzoylmercaptoacetyl)-L-glutamyl-(gamma-methylester)-3-(6-chloropyridazyl)hydrizide
N(-S-benzoylmercaptoacetyl)-glycyl-6-hydrazino nicotinic acid
N-(S-benzoylmercaptoacetyl)-glycyl-6-hydrazino nicotinyl-N-hydroxysuccinimide
N-(S-benzoylmercaptoacetyl)-glycyl-2-pyrimidylhydrazide The substituents represented by $R^9$ and $R^{10}$ together with the adjacent nitrogen atom form a 5- or 6-membered, saturated or unsaturated heterocyclic ring which may be fused to another five or six membered saturated or unsaturated, heterocyclic or carbocyclic ring. Five and six membered heterocyclic rings include but are not limited to pyrole, pyrazole, imidazole, pyridine, pyrazine, pyridazine, pyrimidine and triazine. Fused rings include but are not limited to N-containing bicyclics such as quinoline, isoquinoline, indole and purine. Rings containing sulfur atoms e.g. thiazole, and rings containing oxygen atoms e.g. oxazole are also encompassed by the present invention. Suitable substituents on the heterocyclic ring formed by $R^9$ and $R^{10}$ include from 1–3 groups selected from halogen, carboxyl, carboxy-alkylthio and $C_{1-8}$ alkyl optionally substituted with 1–3 groups selected from hydroxyl, carboxyl, thiocyanato, areinc and hydrazinc groups.

For coupling to a targeting molecule, $R^9$ and $R^{10}$ desirably incorporate a conjugating group. Conjugating groups are chemically reactive groups that allow for coupling of the chelator to a targeting molecule. In the preferred case where the targeting molecule is a peptide or protein, the conjugating group is reactive under conditions that do not denature or otherwise adversely affect its targeting properties. In one embodiment of the invention, the conjugating group is reactive with a functional group of the peptide/protein such as an areinc terminal group or an earninc group of a lysine residue, so that the conjugating reaction can be conducted in a substantially aqueous solution. Useful conjugating groups include but are not limited to groups such as carboxyl, activated esters, carboxy-methylthiols, thiocyanates, amines, hydrazines, maleimides, thiols, and activated halides. In a preferred embodiment of the invention, conjugating groups are selected from methyl propanoate, carboxyl group and N-hydroxysuccinimide ester. Carboxyl conjugating groups may be activated with carbodiimide and an alcohol thereby forming an ester that is reactive with an areinc group available on targeting molecules such as peptides and areinc sugars, to form an amide linkage between the targeting molecule and the chelator conjugating group. For diagnostic imaging purposes, the chelator per se may be used in c, ombination with a metal radionuclide. Suitable radionuclides include technetium and rhenium in their various forms such as $^{99m}TcO^{3+}$, $^{99m}TcO_2^{3o}$, $ReO^{3+}$ and $ReO_2^+$. More desirably, the chelator is coupled through its conjugating group to a targeting molecule to form a conjugate that serves to deliver a chelated radionuclide to a desired location in a mammal. Examples of targeting molecules include, but are not limited to, steroids, proteins, peptides, antibodies, nucleotides and saccharides. Preferred targeting molecules include proteins and peptides, particularly those capable of binding with specificity to cell surface receptors characteristic of a particular pathology. For instance, disease states associated with over-expression of particular protein receptors can be imaged by labeling that protein or a receptor binding fragment thereof in accordance with the present invention. Representative peptides capable of specifically binding to target sites include:

atherosclerotic plaque (SEQ ID NO: 1–12)
YRALVDTLK
RALVDTLK
RALVDTLKFVTQAEGAK
YAKFRETLEDTRDRMY
AKFRETLEDTRDRMY
YAALDLNAVANKIADFEL
AALDLNAVANKIADFEL
YRALVDTLKFVTEQAKGA
RALVDTLKFVTEQAKGA
YRALVDTEFKVKQEAGAK
RALVDTEFKVKQEAGAK
YRALVDTLKFVTQAEGAK infections and atherosclerotic plaque (SEQ ID NO: 13–27)
VGVAPGVGVAPGVGVAPG
VPGVGVPGVGVPGVGVPGVG
formyl.Nleu.LF.Nleu.YK
formylMIFL
formylMLFK
formylMLFI
formylMFIL
formylMFLI
formylMLIF
formylMILF
formylTKPR
VGVAPG formylMLF
YIGSR
CH₂CO.YIGSRC
thrombus (SEQ ID NOS: 28-30)
    NDGDFEEIPEEYLQ
    NDGDFEEI PEEY(SO₃Na)LQ
    GPRG
platelets (SEQ ID NOS: 31-35)
    D-Phe.PRPGGGGNGDFEEIPEEYL
    RRRRRRRRRGDV
    PLYKKIIKKLLES
    RGD
    RGDS
amyloid plaque (Alzheimer's disease) (SEQ ID NO: 37)
    EKPLQNFTLSFR In a particular embodiment of the invention, imaging of inflammation is achieved using a conjugate in which the targeting molecule is a chemotactic peptide comprising the SEQ ID NO: 37) amino acid sequence Thr-Lys-Pro-Pro-Lys (TKPPR). It has been found that this peptide binds particularly well to "Tuftsin" receptors on leukocytes. Targeting peptides can be spaced from the chelator or the conjugating group by additional amino acid residues, preferably glycine, provided the peptide retains its localizing activity. In a particular embodiment, the TKPPR peptide is coupled to chelators of the invention by a Gly residue coupled to the conjugating group.

Peptide-based targeting molecules can be made, either per se or as chelator conjugates, using various established techniques. Because it is amenable to solid phase synthesis employing alternating t-Boc protection and deprotection is the preferred method of making short peptides. Recombinant DNA technology is preferred for producing proteins and long fragments thereof.

Specific chelators of the present invention are those in which $R^9$ and $R^{10}$ form a 6-membered, N-containing heterocyclic ring. In a preferred embodiment, $R^9$ and $R^{10}$ form a pyridine ring attached to the hydrazide moiety at the number 2 position which is the carbon atom adjacent to the nitrogen atom. In another embodiment of the present invention, the ring formed by $R^9$ and $R^{10}$ incorporates a conjugating group such as N-hydroxysuccinimide or more preferably a carboxyl group.

Specific chelators of the present invention can be prepared by the following general procedure. Commercially available N-chloroacetylglycine, or a variant thereof substituted as desired, is reacted with potassium thiobenzoate yielding N-benzoylthioacetyl-glycine. This intermediate is then transformed into the corresponding N-hydroxysuccinimide ester using dicyclocarbodiimide in dioxane. The ester is reacted in dioxane at room temperature with a selected hydrazino substituted ring obtained by reacting the ring with hydrazine. It is understood that the hyrdrazino substituents at the carbon atom adjacent to the coordinating nitrogen atom of the ring are obtained when the ring is substituted at that position with a suitable leaving group, such as chlorine, prior to the reaction with hydrazine. The resulting chelator is then purified by recrystallization. A method of preparing the present chelators is represented below:

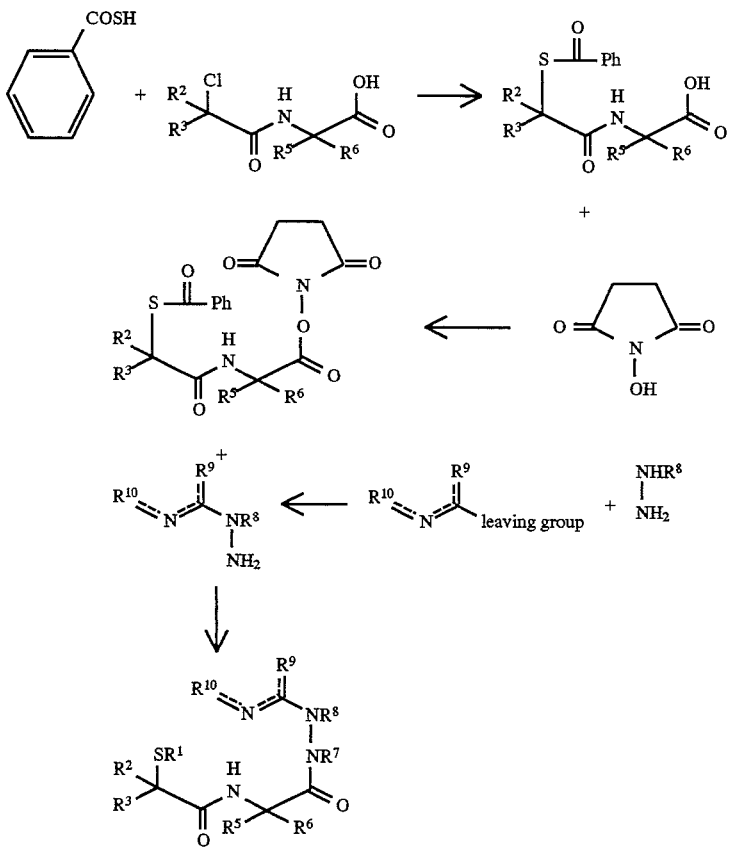

It is to be understood that the present invention encompasses various heterocyclic compounds that contain a nitrogen atom adjacent to the carbon atom attached to the hydrazide substituent. For example, nicotinic acid when reacted with hydrazine yields 6-hydrazino nicotinic acid used to synthesize a metal chelator with a carboxyl group for conjugating a targeting molecule thereto. Other possible rings include but are not limited to five membered rings, bicyclics as well as rings containing additional nitrogen atoms or sulfur or oxygen atoms. Further, it is to be understood that variation at $R^2$ and $R^3$ can be introduced by using derivatives of N-chloroacetyl-glycine. For example, the acetyl portion may have one or two substituents such as lower alkyl ($C_{1-4}$) that may be substituted with from 1–3 groups selected from hydroxyl and carboxyl. Variation at $R^5$ and $R^6$ may be introduced by incorporating any N-chloro D or L amino acid (except proline) in place of glycine or by using glycine substituted with for instance $C_{1-8}$alkyl, hydroxyl, carboxyl group. Alkyl substituents at $R^5$ and $R^6$ may be straight or branched and optionally substituted with from 1–3 halogen atoms, carboxyl, mercapto, areinc or aminocarbonyl groups.

In a particularly preferred embodiment, chelator-peptide conjugates are prepared by solid-phase peptide synthesis methods, which involve the stepwise addition of areinc acid residues to a growing peptide chain that is linked to an insoluble (solid) support or matrix, such as polystyrene. The C-terminus residue of the targeting peptide is first anchored to a commercially available support with its areinc group protected with an N-protecting agent such as a fluorenyl-methoxycarbonyl (FMOC) group. The areinc protecting group is removed with suitable deprotecting agents such as piperidine and the next areinc acid residue (in N-protected form) is added with a coupling agent such as dicyclocarbo-diimide (DCC). Upon formation of a peptide bond, the reagents are washed from the support. After addition of the final residue, the chelator is coupled to the N-terminus of the targeting peptide by the addition first of a synthetically prepared residue of the formula

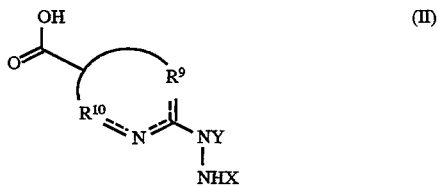

wherein X is H or an aminoprotecting group and Y is $C_{1-4}$ alkyl and then adding both an amino acid residue of the formula —C(O)—C($R^5R^6$)—NHX and mercaptoacetic acid or a derivative of the formula —C(O)—C($R^2R^3$)—$SR^1$, where $R^1$, $R^2$, $R^3$, $R^5$ and $R^6$ are as defined above. It will be appreciated that the chelator may be coupled to the N-terminus of the targeting peptide as a whole or in part ie. where X of the synthetically prepared residue is —C(O)—C($R^5R^6$)—NHZ or —C(O)—C($R^5R^6$)—NH—C($R^2R^3$)—$SR^1$ wherein Z is H or an aminoprotecting group. The synthetic residue of formula (11) is prepared from an N-containing heterocycle which is derivatized with a carboxyl conjugating group and a leaving group adjacent to the coordinating nitrogen atom, for example, commercially available 6-chloronicotinic acid. This is reacted with N-alkyl-hydrazine to form an N-alkyl-hydrazino substituted heterocycle. In a particular embodiment N-methylhydrazine is reacted with 6-chloronicotinic acid to give 6-(N-methyl-hydrazino)nicotinic acid which is employed in the solid phase synthesis as an individual amino acid residue. Following the addition of 6-(N-methylhydrazino)nicotinic acid to the targeting peptide another amino acid residue according to the formula —C(O)—C($R^5R^6$)—NHZ is coupled to the N'-amino group and finally a mercapto acetic acid derivative of the formula —C(O)—C($R^2R^3$)—$SR^1$. After addition of the mercaptoacetic acid residue to the chain the, chelator-conjugate is cleaved from the support with a suitable reagent such as trifluoroacetic acid (TFA).

In a most preferred embodiment of the invention a chelator conjugate is prepared on a solid support and has the structure of formula (I) wherein the targeting molecule is a peptide having a sequence Gly—Thr—Lys—Pro—Pro—Arg—OH, SEQ ID NO: 38 the conjugating group is a carboxyl group substituent on a pyridine ring formed by $R^9$ and $R^{10}$, $R^8$ is methyl, $R^7$ is H, one of $R^5$ and $R^6$ is H and the other is hydroxymethyl, $R^4$ is H, $R^3$ and $R^2$ are both H and $R^1$ is the sulfur protecting group acetamidomethyl.

Incorporation of the selected radionuclide within the chelator can be achieved by various methods. A chelator solution is formed initially by dissolving the chelator in aqueous alcohol eg. ethanol-water 1:1. Oxygen is removed for example by degassing with $N_2$, then sodium hydroxide is added to remove the thiol protecting group. The solution is again purged of oxygen and heated on a water bath to hydrolyze the thiol protecting group, and the solution is then neutralized with an organic acid such as acetic acid (pH 6.0–6.5). In the labeling step, sodium pertechnetate is added to the chelator solution with an amount of stannous chloride sufficient to reduce the technetium. The solution is mixed and left to react at room temperature and then heated on a water bath. In an alternative method, labeling can be accomplished with the chelator solution adjusted to pH 8. At this higher pH, pertechnetate may be replaced with a solution containing technetium complexed with lablie ligands suitable for ligand exchange reactions with the desired chelator. Suitable ligands include tartarate, citrate and heptagluconate. Stannous chloride may be replaced with sodium dithionite as the reducing agent if the chelating solution is alternatively adjusted to a still higher pH of 12–13 for the labeling step. The chelators of the present invention can be coupled to a targeting molecule prior to labeling with the radionuclide, a process referred to as the "bifunctional chelate" method. An alternative approach is the "prelabeled ligand" method in which the chelator is first labeled with a radionuclide and is then coupled to the targeting molecule.

The labeled chelator may be separated from contaminants $^{99m}TcO_4^-$ and colloidal $^{99m}TcO_2$ chromatographically, e.g., with a C-18 Sep Pak column activated with ethanol followed by dilute HCl. Eluting with dilute HCl separates the $^{99m}TcO_4^-$, and eluting with EtCH-saline 1:1 brings off the chelator while colloidal $^{99m}TcO_2$ remains on the column.

When coupled to a targeting molecule and labeled with a diagnostically useful metal, chelators of the present invention can be used to detect pathological conditions by techniques common in the art of diagnostic imaging. A chelator/targeting molecule conjugate labeled with a radionuclide metal such as technetium may be administered 5 to a mammal intralymphatically, intraperitoneally and preferably intravenously in a pharmaceutically acceptable solution such as saline or blood plasma medium. The amount of labeled conjugate administered is dependent upon the toxicity profile of the chosen targetting molecule as well as the profile of the metal and is generally in the range of about 0.01 to 100mCi/70 Kg and preferably 10 to 50mCi/70 Kg host. Localization of the metal in vivo is tracked by standard scintigraphic techniques at an appropriate time, typically at regular intervals between 15 minutes and 24 hours subsequent to administration. In a particular embodiment, chelators of the invention coupled to the peptide TKPPR in a saline solution are administered to a mammal by intravenous injection to image sites of focal inflammation.

The following examples are presented to illustrate certain embodiments of the present invention.

EXAMPLE 1—Preparation of N-(S-benzoylmercaptoacetyl)-glycine

To a stirring solution under argon at 0° C. of (1.50g, 10mmoles) N-chloroacetylglycine in (25 mL) ethanol was added (1.41 ml, 12 mmoles) thiobenzoic acid, followed by (7.0 mL, 3N, 21 mmoles) potassium hydroxide over 3 minutes. The reaction was allowed to heat to room temperature for 20 minutes followed by reflux under argon at 50° C. for 2 hours. The reaction was cooled to room temperature and acidified with (5 mL, 2N) hydrochloric acid. The ethanol was rotavapped off to leave N-(S-benzoylmercaptoacetyl)-glycine (m.p. 140.5°–141.5° C.), a white solid, which was washed with water, filtered, and dried in vacuo (2.46g, 98% yield).

EXAMPLE 2—Preparation of chelator N-(S-benzoylmercaptoacetyl)-glycyl-2-pyridylhydrazide To a stirring solution at 7° C. of (1.10g, 4.35 mmoles) N-(S-benzoylmercaptoacetyl)-glycine and (502 mg, 4.35 mmoles) N-hydroxysuccinimide in (34 mL) dioxane was added a solution of (904 mg, 4.38 mmoles) DCC in (1 mL) dioxane. After the reaction stirred for 5 hours at room temperature it was stored overnight at 4° C. It was then filtered and rotavapped to a white solid. N-(S-benzoylmercaptoacetyl)-glycine N-hydroxy succinimide ester, was triturated with cold isopropanol, filtered, and dried in vacuo to a white solid (1.40 g, 92% yield).

To a stirring solution of (1.50 g, 4.45 mmoles) N-(S-benzoylmercaptoacetyl)-glycyl N-hydroxysuccinimide ester in (30 mL) dioxane under argon was added a solution of (500 mg, 4.45 mmoles) 2-hydrazinopyridine in (6 mL) dioxane. After ½ dioxane was stripped off to a yellow oil. The product (1.46 g, 99%, m.p. 162°–162.5° C.) solidified in (10 mL) aqueous sodium bicarbonate. The product, N(-S-benzoylmercaptoacetyl)-glycyl-2-pyridylhydrazide, was suction filtered and washed with water and then (700 mg) of product was recrystallized from (1:1) ethyl acetate:dioxane (600 mg, 85%).

EXAMPLE 3—Preparation of chelator No(S-benzoylmercaptoacetyl)-L-glutamyl-(gamma-methyl ester)-2-pyridylhydrazide To a stirring solution of (2.73 g, 9.31 mmoles) N-(S-benzoylmercaptoacetyl)-glycyl N-hydroxysuccinimide ester in (50 mL) dioxane was added a solution of (1.50 g, 9.31 mmoles) L-glutamic acid methyl ester and (1.88 g, 18.6 mmoles) triethylamine in (50 mL) dioxane. After 7 hours the dioxane was stripped off and (10 mL) water was added. The solution was acidified to pH 2.5, extracted into ethyl acetate, dried over sodium sulfate, filtered, and rotavapped to yield a pale yellow oil of N-(S-benzoylmercaptoacetyl)-L-glutamic acid methyl ester.

To a stirring solution at room temperature of (9.3 mmole) N-(S-benzoylmercaptoacetyl)-L-glutamic acid methyl ester and (1.07 g, 9.31 mmoles) N-hydroxysuccinimide in (100 mL) dioxane was added a solution of (1.92 g, 9.31 mmoles) DCC in (25 mL) dioxane. After the reaction stirred for 7 hours it was filtered, then rotavapped to a white solid. N-(S-benzoylmercaptoacetyl)-L-glutamyl-(gammaomethyl ester) N-hydroxysuccinimide ester, was triturated with cold isopropanol, filtered and dried in vacuo to a white fluffy solid (3.70 g, 91% yield).

To a stirring solution of (1.00 g, 2.29 mmoles) N-(Sobenzoylmercaptoacetyl)-glutamyl-(gamma-methyl ester) N-hydroxysuccinimide ester in (20 mL) dioxane under argon was added a solution of (250 mg, 2.29 mmoles) 2-hydrazinopyridine in (10 mL) dioxane. After 1 hour dioxane was stripped off to pale yellow oil. The product, N(-S-benzoylmercaptoacetyl)-L-glutamyl-(gamma-methyl ester)-2-pyridylhydrazide (760 mg, 77%) solidified in (5 mL) water. The product (m.p. 162°–163° C.) was suction filtered and washed with water and then recrystallized from (3:1) ethyl acetate: dioxane (200 mg).

EXAMPLE 4—Preparation of chelator N-(S-benzoylmercaptoacetyl)-glycyl-3-(6-chloropyridazyl)-hydrazide A solution of (6.0 g, 40.3 mmoles) 3,6-dichloropyridazine and (4.0 g, 80 mmoles) hydrazine monohydrate in (50 mL) ethanol was refluxed under argon for 3 hours. The solution was cooled to room temp. where it solidified to an off-white solid matrix. 6-chloro-3-hydrazinopyridazine was crushed, washed in (20 mL) water, filtered and then recrystallized from hot water to a white spongy crystal.

To a stirring solution of (845 mg, 2.50 mmoles) N-(S-benzoylmercaptoacetyl)-glycyl N-hydroxysuccinimide ester in (30 mL) dioxane under argon was added (361 mg, 4.45 mmoles) 6-chloro-3-hydrazinopyridazine which slowly dissolved. After 40 minutes a white crystal formed. The product (m.p. 164°–165.5° C.) was suction filtered and washed with a small portion of dioxane and then recrystallized from ethyl acetate: methanol (200 mg).

EXAMPLE 5—Preparation of chelator N-(S-benzoylmercaptoacetyl)-L-glutamyl-(gamma-methylester)-3-(6-chloropyridazyl)-hydrazide A solution of (6.0 g, 40.3 mmoles) 3,6-dichloropyridazine and (4.0 g, 80 mmoles) hydrazine monohydrate in (50 mL) ethanol was refluxed under argon for 3 hours. The solution was cooled to room temp. where it solidified to an off-white solid matrix. 6-chloro-3-hydrazinopyridazine was crushed, washed in (20 mL) water, filtered, and then recrystallized from hot water to a white spongy crystal.

To a stirring solution at room temperature of (2.0 g, 4.58 mmoles) N-(S-benzoylmercaptoacetyl)-L-glutamyl-(gamma-methylester) N-hydroxysuccinimideester in (25 mL) dioxane was added a partially dissolved solution of (662 mg, 4.58 mmoles) 3-(6-chloropyridazyl)-hydrazide in (15 mL) dioxane. After the reaction stirred for 1 hour all starting material had dissolved. The dioxane was rotavapped off to a pale yellow oil. After (5 mL) water was added the oil formed a pale yellow solid. The product (m.p. 164–165) was filtered, washed with water, and dried in vacuo, (1.80 g, 85% yield).

EXAMPLE 6 - Preparation of chelator N-(S-benzoylmercaptoacetyl)-glycyl-6-hydrazino nicotinic acid A solution of (3.00 g, 19 mmoles) 6-chloronicotinic acid and (4.62 mL, 95 mmoles) hydrazine monohydrate in (15 mL) ethanol was refluxed under argon for 18 hours. Upon cooling to room temperature a white solid product, 6-hydrazino nicotinic acid, formed. This was filtered and washed with ethanol then dissolved in water, acidified to pH 7.0 with acetic acid causing a white precipitate. This was filtered, washed with water, and dried in vacuo over KOH, (1.87 g, 64% yield)

To a stirring solution of (460 mg, 3.0 mmoles) 6-hydrazinonicotinic acid and (318 mg, 3.0 mmoles) sodium carbonate in (15 mL) water was dripped a solution of (1.02 g, 3.0 mmoles) N-(S-benzoylmercaptoacetyl)-glycyl N-hydroxysuccinimide ester in (25 mL) dioxane. The reaction began immediately with a yellow color forming. After 1 hour dioxane was rotavapped off to leave (10 ml) water. This was acidified to pH 5.5 with 2 N hydrochloric acid causing a white precipitate to form. The product was filtered, washed with water, and dried in vacuo, (902 mg, 80% yield). Melting point was not obtained as the product decomposed over a large range.

EXAMPLE 7—Preparation of chelator N-(S-benzoylmercaptoacetyl)-glycyl-6-hydrazino nicotinyl-N-hydroxy succinimide To a stirring solution of (376 mg, 1.0 mmoles) N-(S-benzoylmercaptoacetyl)-glycyl-6-hydrazinonicotinic acid and (115.3 mg, 1.0 mmoles) N-hydroxysuccinimide ester in (30 mL) dioxane was added drop-wise a solution of (206 mg, 1.0 mmole) dicyclocarbodiimide in (5 mL) dioxane. The solution was filtered then rotavapped to give a pale yellow semi-solid oil which was triturated with cold isopropanol to give a pale yellow solid. The product was filtered, rinsed with isopropanol, and dried in vacuo. The melting point was found to be 176°–178° C. followed by decomposition.

EXAMPLE 8—Preparation of chelator N-(S-benzoylmercaptoacetyl)-glycyl-2-pyrimidylhydrazide To a stirring solution of (1.00 g, 8.73 mmoles) 2-chloropyrimidine in (3 mL) dioxane under argon was added (1.31 g, 26.2 mmoles) hydrazine monohydrate. The reaction started immediately giving off heat. The solution was refluxed under argon at 60° C. for 2 hours. Upon cooling to room temperature a white solid crystallized out. A mixture of (1:1, 2 mL) dioxane:water was added dissolving the solid. The solvents were rotavapped to about 2 ml of liquid and a white solid. 2-hydrazinopyrimidine (955 mg, 99% yield) was filtered, washed with dioxane, and dried in vacuo.

To a stirring solution of (200 mg, 1.82 mmoles) 2-hydrazinopyrimidine in (25 mL) dioxane was added a solution of (61 5 mg, 1.82 mmoles) N-(S-benzoylmercaptoacetyl)-glycyl-N-hydroxysuccinimide ester in (25 mL) dioxane. The reaction was stirred for 1 hour and the dioxane was rotavapped off to a yellow oil. This was dissolved in isopropanol and rotavapped to a white solid. The solid product (m.p. 176°–178° C.) was washed with aqueous bicarbonate, filtered and dried in vacuo, (510 mg, 84% yield). A small amount (120 mg) was recrystallized from hot methanol.

EXAMPLE 9—Preparation of $^{99m}$Tc labeled chelators

The chelator N-(S-benzoylmercaptoacetyl)-glycyl-2-pyridylhydrazide (example 2, 1 mg) was dissolved in EtOH-water and hydrolyzed by heating with NaOH, after which the reaction mixture was neutralized with acetic acid to pH 6. 350 µg hydrolyzed chelator was reacted with 103 MBq $TcO_4^-$ and 10 µg $SnCl_2$ at room temperature. Approximately half activity was present as $TcO_2$ which did not change after heating 10 minutes at 80° C. To achieve adequate separation of the chelator, the solution was then loaded on a C-18 SepLPak column which was eluted with dilute HCl to remove TcO4-. Subsequent elution with 1:1 EtOH-saline removed the chelator while TcO2 remained on the column.

Another chelator was similarly labeled. Particularly, 300 µg of the hydrolyzed chelator N-(S-benzoylmercaptoacetyl) -glycyl-3-(6-chloropyridazyl)-hydrazide (example 4) was adjusted to pH 12–13 and reduced with 100 µg of sodium dithionite for 10 minutes at 75° C. The resulting mixture was then loaded on a C-18 Sep-Pak column and eluted with dilute HCl followed by EtOH-saline. The extent of complexation of $^{99m}$Tc with chelators was measured by radioactivity of the eluted fractions; results are shown in the table below.

|  | Example 2 | Example 4 |
| --- | --- | --- |
| TcO4- (HCl eluate) | 0.15 (1%) | 1.38 (8%) |
| TcO2 (column) | 12.5 (31%) | 2.55 (14%) |
| Chelator (EtOH-saline eluate) | 27.6 (68%) | 14.19 (78%) |

*units of measure in MBq with corresponding percent of total

EXAMPLE 10—In vivo distribution

Distribution within rats of selected chelators and a reference chelator was determined using established protocols. Briefly, male Wistar rats (Charles River, 200 g) were anesthetized with somnitol (40 to 50 mg/kg) and 200 µL of the labeled chelator (ie. 200 µCi) was injected intravenously via the tail vein. Serial whole-body scintigrams were acquired for first 10 minutes. After further images were obtained at 60 and 120 minutes, the rat was killed with anesthesia and samples of organs (blood, heart, lung, liver, spleen, kidney, muscle, GI tract) were weighed and counted in either a well-type gamma counter or in a gamma dose calibrator. Dose calculations were made based On the assumption that rats weighed 200 g and that the blood volume constituted 8% body weight. All results were corrected for the residual dose in the tail.

The chelators were found to clear relatively rapidly from the blood as desired. For the chelator of example 2, it was found that the liver and GI tract accounted for about 60% of the dose, with only about 6% remaining in the blood. The chelator of example 5 localized primarily (55%) in the GI tract, with only about 10% of the dose remaining in the blood. About 70% of the chelator of example 4 was localized in the liver and GI tract.

Of these chelators, the chelator of example 4 showed the fastest clearance from the blood and other tissues and is mainly eliminated through the liver and GI tract. The chelator of example 3 had the greatest accumulation in the kidney.

The reference chelator, lacking the hydrazide-based structure yet having the $N_3S$ configuration N-(S-benzoylmercaptoacetyl)-glycyl-2-pyridylmethylamide, was extensively retained in the blood pool which would be disadvantageous for imaging as this contributes to higher levels of the radionuclide in all tissues.

EXAMPLE 11—Preparation of Chelator-Peptide Conjugate S-Acm-Mercaptoacetyl-Ser-N-methylhydrazino nicotinic acid- Gly—Thr—Lys—Pro—Pro—Arg The title chelator conjugate was prepared by solid phase peptide synthesis using FMOC chemistry on an FMOC-arginine preloaded 2-methoxy-4-alkoxybenzyl alcohol resin (Sasrin Resin, Bachera Biosciences In., Philadelphia) with an Applied Biosystems 433A peptide synthesizer (Foster City, CA). The synthetically prepared residue 6-(N-methylhydrazino)nicotinic acid and commercially obtained acetamidomethyl-mercaptoacetic acid were incorporated in the peptide by coupling to the Gly and Ser residues respectively.

Synthetic residue 6-(N-methylhydrazino)nicotinic acid was prepared as follows. To a solution of (2.0 g, 12.69 mmole) 6-chloronicotinic acid in (15 mL) ethanol was added (1.38 mL, 26 mmole) N-methylhydrazine. The reaction was refluxed under argon for 2 days where the resulting precipitate, 6-(N-methylhydrazino)nicotinic acid, was collected, washed with 10 mL ethanol, and dried in vacuo to a white solid (1.34 g, 63.3%).

The N'-amino group of 6-(N-methylhydrazino)nicotinic acid was FMOC protected as follows. To a solution of (500 mg, 2.99 mmole) 6-(N-methylhydrazino)nicotinic acid in (1 N, 45 mL) aqueous potassium carbonate and (55 mL) dioxane at 0° C. was added dropwise a solution of (1.22 g, 4.71 mmole) FMOC-chloride in 5 mL dioxane. The solution was warmed to room temp. and stirred for 8 hours and then rotavapped to 30mU 50 mL water was added to the solution and then washed with (2×40 mL) diethyl ether. The aqueous phase was acidified with 1N HCl to pH 5 and the solution was extracted with (3×50 mL) ethyl acetate and 6-(N'-FMOC, N-methylhydrazino)nicotinic acid was dried over $MgSO_4$, filtered and rotavapped to an off white solid (680 mg, 73.5%).

The peptide-resin was dried under vacuum overnight and cleavage of the peptide from the resin was achieved by mixing a cooled solution of 9.5 mL trifluoroacetic acid (TFA), 0.5 mL water, 0.5 mL thioanisole and 0.25 mL 2-ethanedithiol (1 mL per 100 mg of peptide-resin) with the peptide-resin for 1.5 to 2 hours at room temperature. The resin was removed by filtration and washed with 1–3 mL of TFA to obtain 6–8 mL of a clear yellow liquid. This liquid was slowly dropped into 30–35 mL of cold tert-butyl ether in a 50 mL conical polypropylene centrifuge tube forming a white precipitate. The precipitate was centrifuged at 7000rpm, 0° C. for 5 minutes (Sorvall RT6000, Dupont), decanted and washed two more times with tert-butyl ether. Following drying under vacuum the precipitate was dissolved in water. The precipitate was frozen in acetone-dry ice and lyophilized overnight. The resulting white powder was dissolved in water, filtered through a 0.45 μm syringe filter (Gelman Acrodisc 3 CR PTFE), and purified by reversed-phase HPLC (Beckman System Gold) with a C18 column (Waters RCM 25×10) using 1% TFA in water as buffer A and 1% TFA in acetonitrile as buffer B. The column was equilibrated with 100:0 buffer A:buffer B and eluted with a linear gradient in 25 minutes at 1 mL/min to 50% buffer B. Fractions were reanalysed on the HPLC and pooled according to matching profiles. The pure fractions were frozen in acetone-dry ice and lyophilized overnight to give a white powder.

EXAMPLE 12—Labeling of Chelator-Conjugate S-Acm-Mercaptoacetyl-Ser-N-methylhydrazino nicotinic acid-Gly—Thr—Lys—Pro—Pro—Arg SEQ ID NO: 39)

The chelator-conjugate of example 11 (200 μL, 1 mg/mL saline) was injected into a 3 mL vacutainer with 100 μL pertechnetate (10 mCi) and 100 μL stannous gluconate (50 μg stannous chloride and 1 mg sodium gluconate). The tube was placed in a boiling water bath for 12 minutes and then filtered through a Watman PVDF syringe filter to collect the labeled conjugate solution which was further diluted with saline to prepare an injectable solution (2 Mbq/mL). The chelator-conjugate was isolated by HPLC (Beckman) from a (20 μL) sample (before dilution) to determine the labeling yield by measuring radioactivity of the fractions. 70.8%, 5.1% and 15.0% of the label was found in each of three fractions eluted for a 90.9% total labeling yield.

We claim:
1. A compound of the general formula:

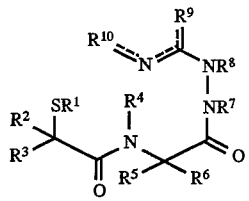

wherein

R¹ is H or a sulfur protecting group;

R² and R³ are selected independently from H; carboxyl; lower alkyl; and lower alkyl substituted with a group selected from hydroxyl, sulfhydryl, halogen, carboxyl and aminocarbonyl;

R⁴ and R⁷ are each H;

R⁵ and R⁶ are selected independently from H; carboxyl; lower alkyl; lower alkyl substituted with a group selected from hydroxyl, sulfhydryl, halogen, carboxyl, lower alkoxycarbonyl and aminocarbonyl; and an alpha carbon side chain of any amino acid other than proline;

R⁸ is selected from H, carboxyl, lower alkyl and lower alkyl substituted with hydroxyl, carboxyl or halogen; and R⁹ and R¹⁰ together form a 5- or 6-membered, saturated or unsaturated heterocyclic ring which is optionally fused to another 5- or 6-membered saturated or unsaturated, heterocyclic or carbocyclic ring wherein either ring is optionally substituted with a group selected from halogen, alkyl, hydroxyalkyl, carboxyl, carboxyalkyl, carboxyalkylthio, thiocyanato, amino, hydrazino and a conjugating group for coupling a targeting molecule to said either ring.

2. A compound according to claim 1 wherein R², R³, R⁴, R⁵, R⁷ and R⁸ are hydrogen.

3. A compound according to claim 2 wherein R⁹ and R¹⁰ together form a pyridine ring.

4. A compound according to claim 2 wherein R⁹ and R¹⁰ together form a pyrimidine ring.

5. A compound according to claim 2 wherein R⁹ and R¹⁰ together form a 3-chloro substituted pyridazine ring.

6. A compound according to claim 2 wherein R⁹ and R¹⁰ together form a 5-carboxy substituted pyridine ring.

7. A compound according to claim 2 wherein R⁹ and R¹⁰ together form a 5-N-hydroxysuccinimide carboxy substituted pyridine ring.

8. A compound according to claim 2 wherein R⁹ and R¹⁰ together form a 3-chloro substituted pyridazine ring and R₆ is the group CH₂CH₂COOMe.

9. A compound according to claim 2, wherein R⁹ and R¹⁰ together form a pyridine ring and R₆ is the group CH₂CH₂COOMe.

10. A compound according to claim 1, wherein R¹ is selected from the group consisting of a hydrogen atom, benzoyl group, acetamidomethyl group and a substituted or unsubstituted tetrahydropyranyl group.

11. A compound according to claim 1, wherein R⁹ and R¹⁰ form a ring substituted by a conjugating group for coupling a targeting molecule to said other ring.

12. A compound according to claim 11, wherein the conjugating group is selected from the group consisting of carboxyl, N-hydroxysuccinimide ester and methyl propanoate.

13. A compound according to claim 11, wherein R², R³, R⁴, R⁵, R⁷ and R⁸ are hydrogen.

14. A compound according to claim 13, wherein the ring formed by R⁹ and R¹⁰ is a six membered heterocyclic ring.

15. A compound according to claim 13, wherein R⁹ and R¹⁰ together form a 5-chloro substituted pyridazine ring.

16. A compound according to claim 13, wherein R⁹ and R¹⁰ together form a 5-carboxy substituted pyridine ring.

17. A compound according to claim 13, wherein R⁹ and R¹⁰ together form a 5-N-hydroxysuccinimide carboxy substituted pyridine ring.

18. A compound according to claim 13, wherein R⁹ and R¹⁰ together form a 3-chloro substituted pyridazine ring and R⁶ is the group CH₂CH₂COOMe.

19. A compound according to claim 13 wherein R⁹ and R¹⁰ together form a pyridine ring and R⁶ is the group CH₂CH₂COOMe.

20. A compound according to claim 11, wherein R¹ is selected from the group consisting of a hydrogen atom, benzoyl group, acetamidomethyl group or a substituted or unsubstituted tetrahydropyranyl group.

21. A compound according to claim 11, wherein a targeting molecule is coupled to said conjugating group.

22. A compound according to claim 21, wherein the targeting molecule is a peptide.

23. A compound according to claim 1, in a form complexed with a metal radionuclide or an oxide or nitride thereof.

24. A compound according to claim 23, in a form complexed with ⁹⁹ᵐTc or oxide thereof.

25. A compound according to claim 21, in a form complexed with a metal radionuclide or an oxide or nitride thereof.

26. A compound according to claim 25, in a form complexed with ⁹⁹ᵐTc or oxide thereof.

27. A compound according to claim 22, wherein the peptide comprises the sequence TKPPR.

28. A compound according to claim 27, wherein the conjugating group is a carboxyl group.

29. A compound according to claim 28, having the formula

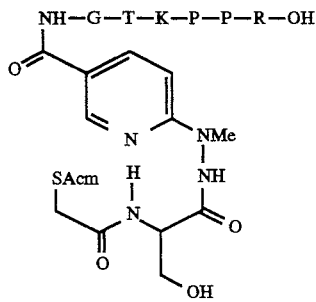

30. A compound according to claim 29, in a form complexed with a metal radionuclide or an oxide or nitride thereof.

31. A compound according to claim 30, wherein said metal radionuclide is $^{99m}$Tc.

32. A method of preparing a compound according to claim 22, wherein the conjugating group is a carboxyl group and $R^8$ is $C_{1-4}$ alkyl, the method comprising the step of coupling the targeting peptide to an intermediate of the formula

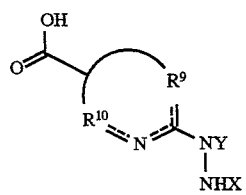

wherein

X is H, an aminoprotecting group, —C(O)—C($R^5R^6$)—NHZ, or —C(O)—C($R^5R^6$)—NH—C(O)—C($R^2R^3$)—$SR^1$;

Y is $C_{1-4}$ alkyl; and

Z is H or an aminoprotecting group.

33. The method according to claim 32, wherein the C-terminus of the targeting peptide is immobilized on a solid support.

* * * * *

SEQUENCE LISTING ( 1 ) GENERAL INFORMATION:

( i i i ) NUMBER OF SEQUENCES: 39

( 2 ) INFORMATION FOR SEQ ID NO:1:

( i ) SEQUENCE CHARACTERISTICS:
      ( A ) LENGTH: 9 amino acids
      ( B ) TYPE: amino acid
      ( C ) STRANDEDNESS: single
      ( D ) TOPOLOGY: linear ( x i ) SEQUENCE DESCRIPTION: SEQ ID NO:1:

Tyr  Arg  Ala  Leu  Val  Asp  Thr  Leu  Lys
 1                  5

( 2 ) INFORMATION FOR SEQ ID NO:2:

( i ) SEQUENCE CHARACTERISTICS:
      ( A ) LENGTH: 8 amino acids
      ( B ) TYPE: amino acid
      ( C ) STRANDEDNESS: single
      ( D ) TOPOLOGY: linear ( x i ) SEQUENCE DESCRIPTION: SEQ ID NO:2:

Arg  Ala  Leu  Val  Asp  Thr  Leu  Lys
 1                  5

( 2 ) INFORMATION FOR SEQ ID NO:3:

( i ) SEQUENCE CHARACTERISTICS:
      ( A ) LENGTH: 17 amino acids
      ( B ) TYPE: amino acid
      ( C ) STRANDEDNESS: single
      ( D ) TOPOLOGY: linear ( x i ) SEQUENCE DESCRIPTION: SEQ ID NO:3:

Arg  Ala  Leu  Val  Asp  Thr  Leu  Lys  Phe  Val  Thr  Gln  Ala  Glu  Gly  Ala
 1                  5                  10                 15
Lys ( 2 ) INFORMATION FOR SEQ ID NO:4:

( i ) SEQUENCE CHARACTERISTICS:
        ( A ) LENGTH: 16 amino acids
        ( B ) TYPE: amino acid
        ( C ) STRANDEDNESS: single
        ( D ) TOPOLOGY: linear ( x i ) SEQUENCE DESCRIPTION: SEQ ID NO:4:

```
Tyr Ala Lys Phe Arg Glu Thr Leu Glu Asp Thr Arg Asp Arg Met Tyr
 1               5                  10                  15
```

( 2 ) INFORMATION FOR SEQ ID NO:5:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( x i ) SEQUENCE DESCRIPTION: SEQ ID NO:5:

```
Ala Lys Phe Arg Glu Thr Leu Glu Asp Thr Arg Asp Arg Met Tyr
 1               5                  10                  15
```

( 2 ) INFORMATION FOR SEQ ID NO:6:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( x i ) SEQUENCE DESCRIPTION: SEQ ID NO:6:

```
Tyr Ala Ala Leu Asp Leu Asn Ala Val Ala Asn Lys Ile Ala Asp Phe
 1               5                  10                  15
Glu Leu
```

( 2 ) INFORMATION FOR SEQ ID NO:7:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( x i ) SEQUENCE DESCRIPTION: SEQ ID NO:7:

```
Ala Ala Leu Asp Leu Asn Ala Val Ala Asn Lys Ile Ala Asp Phe Glu
 1               5                  10                  15
Leu
```

( 2 ) INFORMATION FOR SEQ ID NO:8:

( i ) SEQUENCE CHARACTERISTICS:
        ( A ) LENGTH: 18 amino acids
        ( B ) TYPE: amino acid
        ( C ) STRANDEDNESS: single
        ( D ) TOPOLOGY: linear ( x i ) SEQUENCE DESCRIPTION: SEQ ID NO:8:

```
Tyr Arg Ala Leu Val Asp Thr Leu Lys Phe Val Thr Glu Gln Ala Lys
 1               5                  10                  15
Gly Ala
```

( 2 ) INFORMATION FOR SEQ ID NO:9:

( i ) SEQUENCE CHARACTERISTICS:
        ( A ) LENGTH: 17 amino acids 5,659,041

( B ) TYPE: amino acid
( C ) STRANDEDNESS: single
( D ) TOPOLOGY: linear ( x i ) SEQUENCE DESCRIPTION: SEQ ID NO:9:

Arg Ala Leu Val Asp Thr Leu Lys Phe Val Thr Glu Gln Ala Lys Gly
1               5                   10                  15
Ala ( 2 ) INFORMATION FOR SEQ ID NO:10:

( i ) SEQUENCE CHARACTERISTICS:
( A ) LENGTH: 18 amino acids
( B ) TYPE: amino acid
( C ) STRANDEDNESS: single
( D ) TOPOLOGY: linear ( x i ) SEQUENCE DESCRIPTION: SEQ ID NO:10:

Tyr Arg Ala Leu Val Asp Thr Glu Phe Lys Val Lys Gln Glu Ala Gly
1               5                   10                  15
Ala Lys ( 2 ) INFORMATION FOR SEQ ID NO:11:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( x i ) SEQUENCE DESCRIPTION: SEQ ID NO:11:

Arg Ala Leu Val Asp Thr Glu Phe Lys Val Lys Gln Glu Ala Gly Ala
1               5                   10                  15
Lys ( 2 ) INFORMATION FOR SEQ ID NO:12:

( i ) SEQUENCE CHARACTERISTICS:
( A ) LENGTH: 18 amino acids
( B ) TYPE: amino acid
( C ) STRANDEDNESS: single
( D ) TOPOLOGY: linear ( x i ) SEQUENCE DESCRIPTION: SEQ ID NO:12:

Tyr Arg Ala Leu Val Asp Thr Leu Lys Phe Val Thr Gln Ala Glu Gly
1               5                   10                  15
Ala Lys ( 2 ) INFORMATION FOR SEQ ID NO:13:

( i ) SEQUENCE CHARACTERISTICS:
( A ) LENGTH: 18 amino acids
( B ) TYPE: amino acid
( C ) STRANDEDNESS: single
( D ) TOPOLOGY: linear ( x i ) SEQUENCE DESCRIPTION: SEQ ID NO:13:

Val Gly Val Ala Pro Gly Val Gly Val Ala Pro Gly Val Gly Val Ala
1               5                   10                  15
Pro Gly ( 2 ) INFORMATION FOR SEQ ID NO:14:

( i ) SEQUENCE CHARACTERISTICS:
( A ) LENGTH: 20 amino acids (B) TYPE: amino acid
            (C) STRANDEDNESS: single
            (D) TOPOLOGY: linear (x i) SEQUENCE DESCRIPTION: SEQ ID NO:14:

Val Pro Gly Val Gly Val Pro Gly Val Gly Val Pro Gly Val Gly Val
   1               5                   10                  15

Pro Gly Val Gly
               20

(2) INFORMATION FOR SEQ ID NO:15:

(i) SEQUENCE CHARACTERISTICS:
            (A) LENGTH: 9 amino acids
            (B) TYPE: amino acid
            (C) STRANDEDNESS: single
            (D) TOPOLOGY: linear (i x) FEATURE:
            (A) NAME/KEY: Modified-site
            (B) LOCATION: 1
            (D) OTHER INFORMATION: /product="OTHER"
                  / note= "The Xaa at position 1 = formyl"

(i x) FEATURE:
            (A) NAME/KEY: Modified-site
            (B) LOCATION: 2
            (D) OTHER INFORMATION: /product="OTHER"
                  / note= "The Xaa at position 2 = nitrogen"

(i x) FEATURE:
            (A) NAME/KEY: Modified-site
            (B) LOCATION: 6
            (D) OTHER INFORMATION: /product="OTHER"
                  / note= "The Xaa at position 6 = nitrogen"

(x i) SEQUENCE DESCRIPTION: SEQ ID NO:15:

Xaa Xaa Leu Leu Phe Xaa Leu Tyr Lys
      1               5

(2) INFORMATION FOR SEQ ID NO:16:

(i) SEQUENCE CHARACTERISTICS:
            (A) LENGTH: 5 amino acids
            (B) TYPE: amino acid
            (C) STRANDEDNESS: single
            (D) TOPOLOGY: linear (i x) FEATURE:
            (A) NAME/KEY: Modified-site
            (B) LOCATION: 1
            (D) OTHER INFORMATION: /product="OTHER"
                  / note= "The Xaa at position 1 = formyl"

(x i) SEQUENCE DESCRIPTION: SEQ ID NO:16:

Xaa Met Ile Phe Leu
      1               5

(2) INFORMATION FOR SEQ ID NO:17:

(i) SEQUENCE CHARACTERISTICS:
            (A) LENGTH: 5 amino acids
            (B) TYPE: amino acid
            (C) STRANDEDNESS: single
            (D) TOPOLOGY: linear (i x) FEATURE:
            (A) NAME/KEY: Modified-site
            (B) LOCATION: 1
            (D) OTHER INFORMATION: /product="OTHER"
                  / note= "The Xaa at position 1 = formyl"

(x i) SEQUENCE DESCRIPTION: SEQ ID NO:17:

Xaa Met Leu Phe Lys
1               5

( 2 ) INFORMATION FOR SEQ ID NO:18:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="OTHER"
            / note= "The Xaa at position 1 = formyl"

( x i ) SEQUENCE DESCRIPTION: SEQ ID NO:18:

Xaa Met Leu Phe Ile
1               5

( 2 ) INFORMATION FOR SEQ ID NO:19:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="OTHER"
            / note= "The Xaa at position 1 = formyl"

( x i ) SEQUENCE DESCRIPTION: SEQ ID NO:19:

Xaa Met Phe Ile Leu
1               5

( 2 ) INFORMATION FOR SEQ ID NO:20:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="OTHER"
            / note= "The Xaa at position 1 = formyl"

( x i ) SEQUENCE DESCRIPTION: SEQ ID NO:20:

Xaa Met Phe Leu Ile
1               5

( 2 ) INFORMATION FOR SEQ ID NO:21:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="OTHER"
            / note= "The Xaa at position 1 = formyl"

( x i ) SEQUENCE DESCRIPTION: SEQ ID NO:21:

```
    Xaa  Met  Leu  Ile  Phe
    1                   5
```

( 2 ) INFORMATION FOR SEQ ID NO:22:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="OTHER"
            / note= "The Xaa at position 1 = formyl"

( x i ) SEQUENCE DESCRIPTION: SEQ ID NO:22:

```
    Xaa  Met  Ile  Leu  Phe
    1                   5
```

( 2 ) INFORMATION FOR SEQ ID NO:23:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="OTHER"
            / note= "The Xaa at position 1 = formyl"

( x i ) SEQUENCE DESCRIPTION: SEQ ID NO:23:

```
    Xaa  Thr  Lys  Pro  Arg
    1                   5
```

( 2 ) INFORMATION FOR SEQ ID NO:24:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:24:

```
    Val  Gly  Val  Ala  Pro  Gly
    1                   5
```

( 2 ) INFORMATION FOR SEQ ID NO:25:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="OTHER"
            / note= "The Xaa at position 1 = formyl"

( x i ) SEQUENCE DESCRIPTION: SEQ ID NO:25:

```
    Xaa  Met  Leu  Phe
    1
```

( 2 ) INFORMATION FOR SEQ ID NO:26:

(i) SEQUENCE CHARACTERISTICS:
    (A) LENGTH: 5 amino acids
    (B) TYPE: amino acid
    (C) STRANDEDNESS: single
    (D) TOPOLOGY: linear (xi) SEQUENCE DESCRIPTION: SEQ ID NO:26:

Tyr Ile Gly Ser Arg
1               5

(2) INFORMATION FOR SEQ ID NO:27:

(i) SEQUENCE CHARACTERISTICS:
    (A) LENGTH: 7 amino acids
    (B) TYPE: amino acid
    (C) STRANDEDNESS: single
    (D) TOPOLOGY: linear (ix) FEATURE:
    (A) NAME/KEY: Modified-site
    (B) LOCATION: 1
    (D) OTHER INFORMATION: /product="OTHER"
        / note= "The Xaa at position 1 = CH2CO"

(xi) SEQUENCE DESCRIPTION: SEQ ID NO:27:

Xaa Tyr Ile Gly Ser Arg Cys
1               5

(2) INFORMATION FOR SEQ ID NO:28:

(i) SEQUENCE CHARACTERISTICS:
    (A) LENGTH: 14 amino acids
    (B) TYPE: amino acid
    (C) STRANDEDNESS: single
    (D) TOPOLOGY: linear (xi) SEQUENCE DESCRIPTION: SEQ ID NO:28:

Asn Asp Gly Asp Phe Glu Glu Ile Pro Glu Glu Tyr Leu Gln
1               5                   10

(2) INFORMATION FOR SEQ ID NO:29:

(i) SEQUENCE CHARACTERISTICS:
    (A) LENGTH: 15 amino acids
    (B) TYPE: amino acid
    (C) STRANDEDNESS: single
    (D) TOPOLOGY: linear (ix) FEATURE:
    (A) NAME/KEY: Modified-site
    (B) LOCATION: 13
    (D) OTHER INFORMATION: /product="OTHER"
        / note= "The Xaa at position 13 = SO3Na"

(xi) SEQUENCE DESCRIPTION: SEQ ID NO:29:

Asn Asp Gly Asp Phe Glu Glu Ile Pro Glu Glu Tyr Xaa Leu Gln
1               5                   10                  15

(2) INFORMATION FOR SEQ ID NO:30:

(i) SEQUENCE CHARACTERISTICS:
    (A) LENGTH: 4 amino acids
    (B) TYPE: amino acid
    (C) STRANDEDNESS: single
    (D) TOPOLOGY: linear (xi) SEQUENCE DESCRIPTION: SEQ ID NO:30:

Gly Pro Arg Gly
1

( 2 ) INFORMATION FOR SEQ ID NO:31:

( i ) SEQUENCE CHARACTERISTICS:
    ( A ) LENGTH: 20 amino acids
    ( B ) TYPE: amino acid
    ( C ) STRANDEDNESS: single
    ( D ) TOPOLOGY: linear ( i x ) FEATURE:
    ( A ) NAME/KEY: Modified-site
    ( B ) LOCATION: 1
    ( D ) OTHER INFORMATION: /product="OTHER"
          / note= "The Xaa at position 1 = D-Phe"

( x i ) SEQUENCE DESCRIPTION: SEQ ID NO:31:

Xaa Pro Arg Pro Gly Gly Gly Gly Asn Gly Asp Phe Glu Glu Ile Pro
1               5                   10                  15
Glu Glu Tyr Leu
         20

( 2 ) INFORMATION FOR SEQ ID NO:32:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( x i ) SEQUENCE DESCRIPTION: SEQ ID NO:32:

Arg Arg Arg Arg Arg Arg Arg Arg Arg Gly Asp Val
1               5                   10

( 2 ) INFORMATION FOR SEQ ID NO:33:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: linear ( x i ) SEQUENCE DESCRIPTION: SEQ ID NO:33:

Pro Leu Tyr Lys Lys Ile Ile Lys Lys Leu Leu Glu Ser
1               5                   10

( 2 ) INFORMATION FOR SEQ ID NO:34:

( i ) SEQUENCE CHARACTERISTICS:
    ( A ) LENGTH: 3 amino acids
    ( B ) TYPE: amino acid
    ( C ) STRANDEDNESS: single
    ( D ) TOPOLOGY: linear ( x i ) SEQUENCE DESCRIPTION: SEQ ID NO:34:

Arg Gly Asp
1

( 2 ) INFORMATION FOR SEQ ID NO:35:

( i ) SEQUENCE CHARACTERISTICS:
    ( A ) LENGTH: 4 amino acids
    ( B ) TYPE: amino acid
    ( C ) STRANDEDNESS: single
    ( D ) TOPOLOGY: linear ( x i ) SEQUENCE DESCRIPTION: SEQ ID NO:35:

Arg Gly Asp Ser
1

( 2 ) INFORMATION FOR SEQ ID NO:36:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( x i ) SEQUENCE DESCRIPTION: SEQ ID NO:36:

```
Glu  Lys  Pro  Leu  Gln  Asn  Phe  Thr  Leu  Ser  Phe  Arg
 1                  5                        10
```

( 2 ) INFORMATION FOR SEQ ID NO:37:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( x i ) SEQUENCE DESCRIPTION: SEQ ID NO:37:

```
Thr  Lys  Pro  Pro  Arg
 1                   5
```

( 2 ) INFORMATION FOR SEQ ID NO:38:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( x i ) SEQUENCE DESCRIPTION: SEQ ID NO:38:

```
Gly  Thr  Lys  Pro  Pro  Arg
 1                  5
```

( 2 ) INFORMATION FOR SEQ ID NO:39:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="OTHER"
            / note= "The Xaa at position 1 = sulphur"

( i x ) FEATURE:
        ( A ) NAME/KEY: Modified-site
        ( B ) LOCATION: 2
        ( D ) OTHER INFORMATION: /product="OTHER"
            / note= "The Xaa at position 2 = Acm"

( i x ) FEATURE:
        ( A ) NAME/KEY: Modified-site
        ( B ) LOCATION: 3
        ( D ) OTHER INFORMATION: /product="OTHER"
            / note= "The Xaa at position 3 = Mercaptoacetyl"

( i x ) FEATURE:
        ( A ) NAME/KEY: Modified-site
        ( B ) LOCATION: 5
        ( D ) OTHER INFORMATION: /product="OTHER"
            / note= "The Xaa at position 5 = nitrogen"

( i x ) FEATURE:
        ( A ) NAME/KEY: Modified-site
        ( B ) LOCATION: 6
        ( D ) OTHER INFORMATION: /product="OTHER"
            / note= "The Xaa at position 6 = methylhydrazino
                nicotinic acid"

( x i ) SEQUENCE DESCRIPTION: SEQ ID NO:39:

Xaa Xaa Xaa Ser Xaa Xaa Gly Thr Lys Pro Pro Arg
1               5                   10